(12) United States Patent
Seidel

(10) Patent No.: US 11,278,566 B2
(45) Date of Patent: Mar. 22, 2022

(54) AGENT FOR USE FOR INFLAMMATORY CONDITIONS OF MUCOUS MEMBRANES

(71) Applicant: Dietrich Seidel, Feldafing (DE)

(72) Inventor: Dietrich Seidel, Feldafing (DE)

( * ) Notice: Subject to any disclaimer, the term of this patent is extended or adjusted under 35 U.S.C. 154(b) by 0 days.

(21) Appl. No.: 16/091,823

(22) PCT Filed: Apr. 7, 2017

(86) PCT No.: PCT/EP2017/058429
§ 371 (c)(1),
(2) Date: Nov. 30, 2018

(87) PCT Pub. No.: WO2017/174796
PCT Pub. Date: Oct. 12, 2017

(65) Prior Publication Data
US 2019/0125783 A1 May 2, 2019

(30) Foreign Application Priority Data
Apr. 8, 2016 (DE) .................... 10 2016 205 950.5

(51) Int. Cl.
| | | |
|---|---|---|
| A61K 31/785 | (2006.01) | |
| A61K 9/00 | (2006.01) | |
| A61K 9/06 | (2006.01) | |
| A61K 8/81 | (2006.01) | |
| A61Q 5/02 | (2006.01) | |
| A61Q 17/00 | (2006.01) | |
| A61Q 11/00 | (2006.01) | |
| A61Q 19/00 | (2006.01) | |
| A61Q 19/08 | (2006.01) | |
| A61Q 19/10 | (2006.01) | |
| A61K 8/9789 | (2017.01) | |
| A61K 45/06 | (2006.01) | |

(52) U.S. Cl.
CPC .......... *A61K 31/785* (2013.01); *A61K 8/8117* (2013.01); *A61K 8/9789* (2017.08); *A61K 9/006* (2013.01); *A61K 9/0034* (2013.01); *A61K 9/0063* (2013.01); *A61K 9/06* (2013.01); *A61K 45/06* (2013.01); *A61Q 5/02* (2013.01); *A61Q 11/00* (2013.01); *A61Q 17/005* (2013.01); *A61Q 19/00* (2013.01); *A61Q 19/08* (2013.01); *A61Q 19/10* (2013.01); *A61K 2800/522* (2013.01); *A61K 2800/74* (2013.01); *A61K 2800/75* (2013.01)

(58) Field of Classification Search
None
See application file for complete search history.

(56) References Cited

U.S. PATENT DOCUMENTS

| | | | |
|---|---|---|---|
| 4,837,255 A * | 6/1989 | Dechow ............... | A61K 9/0056 424/439 |
| 2003/0095925 A1* | 5/2003 | Dugger, III .......... | A61K 9/0056 424/43 |
| 2005/0032788 A1* | 2/2005 | Wagle .................. | A61K 31/535 514/227.5 |
| 2014/0271491 A1 | 9/2014 | Gittard et al. | |
| 2015/0037320 A1 | 2/2015 | McGrath et al. | |
| 2015/0265611 A1* | 9/2015 | Fujihara ............... | A61K 9/2054 514/254.04 |

FOREIGN PATENT DOCUMENTS

| | | | |
|---|---|---|---|
| DE | 2920071 A1 | 11/1980 | |
| DE | 3930206 A1 | 3/1991 | |
| DE | 69011353 T2 | 12/1994 | |
| DE | 202014009184 U1 | 12/2014 | |
| EP | 1053747 A2 | 11/2000 | |
| EP | 2683418 B1 * | 1/2016 | ....... A61F 13/00063 |
| GB | 2021949 A | 12/1979 | |
| RU | 2355420 C2 | 5/2009 | |
| SU | 825074 A1 | 4/1981 | |
| WO | 9802136 A1 | 1/1998 | |
| WO | 9915186 A1 | 4/1999 | |
| WO | 2012123363 A1 | 9/2012 | |

OTHER PUBLICATIONS

Souza et al (Seminars in Dysphagia, Chapter 1, Section 2.1, 2015) (Year: 2015).*
Ebersole et al (Periodontol 2000, 2013, 62(1), 163-202). (Year: 2013).*
Highfield et al (Australian Dental Journal, 2009, 54:(Suppl): S11-S26). (Year: 2009).*
Kerkadi, et al.: "Dietary Cholestyramine Reduces Ochratoxin A—Induced Nephrotoxicity in the Rat by Decreasing Plasma Levels and Enhancing Fecal Excretion of the Toxin", J. Toxicology and Environmental Health, Part A, 53 (1998), pp. 231-250.
Rankin, et al.: Treatment of Cyanobacterial (Microcyctin) Toxicosis Ucing Oral Cholestyramine: Case Report of a Dog from Montana, J. Toxins 5 (2013), pp. 1051-1063.
Stroehlein, John R.: "Treatment of Costridium difficile Infection", Current Treatment Options in Gastroenterology 7(3) (2004), pp. 235-239.
Taylor, et al.: "Retention of oral microorganisms on cobalt-chromium alloy and dental acrylic resin with different surface finishes", J. of Prosthetic Dentistry 80(5) (1998), pp. 592-297.

* cited by examiner

*Primary Examiner* — Celeste A Roney
(74) *Attorney, Agent, or Firm* — Norton Rose Fulbright US LLP; James R. Crawford

(57) ABSTRACT

The present invention relates to an agent comprising anion-exchange groups that are suitable for adsorbing bacterial lipopolysaccharides (LPS) and/or lipoteichoic acids (LTA), for use in the prevention and/or treatment of inflammatory conditions and/or diseases of the oral cavity or in the vaginal region. The present invention also relates to a pharmaceutical composition that comprises an agent of this kind and can adhere to mucosa.

19 Claims, No Drawings

AGENT FOR USE FOR INFLAMMATORY CONDITIONS OF MUCOUS MEMBRANES

RELATED APPLICATIONS

This application is a § 371 of International Application No. PCT/EP2017/058429 filed Apr. 7, 2017, and claims priority from German Patent Application No. 10 2016 205 950.5 filed Apr. 8, 2016, each of which is incorporated herein by reference in its entirety for all purposes.

The present invention relates to a composition for use in the prevention and/or treatment of inflammatory conditions and/or diseases of mucous membranes, in particular in the region of the oral cavity.

The oral cavity is the beginning of the digestive tract. It is lined with a mucous membrane, referred to as the oral mucosa, and is colonised by a variety of microorganisms, which the oral cavity offers favourable living conditions. Firstly, the oral cavity is a space at a constant and relatively high temperature and is also distinguished by high moisture levels. Secondly, food is taken in via the oral cavity, meaning that there is also a continuous input of nutrients in this space. Since there are difficult-to-access confined spaces, e.g. between the teeth, food residues may accumulate, and these form a nutrient base that favours microbial growth. The oral cavity thus provides suitable conditions for microorganism multiplication.

In healthy people, the microflora of the oral cavity is in a natural equilibrium. In this respect, in normal cases, no particular species of microorganisms undergo excessive multiplication, nor are foreign pathogenic microorganisms able to colonise the area. In cases where the oral mucosa can no longer fulfil its natural barrier role, e.g. due to injuries or as a result of inflammations in the oral mucosa, microorganisms may come into contact with deeper tissue areas and cause an infection, which is initially local in most cases. As a result, defence mechanisms of the organism are initiated or intensified and an inflammatory reaction, which is initially local in most cases, is produced. This reaction can spread to adjacent tissue and even lead to chronic inflammatory conditions. In adverse cases, a local infection of this kind may even spread to become systemic. There is also a known relationship between infections in the oral cavity and simultaneous development of atherosclerosis or an elevated risk of heart attack, rheumatic diseases or diabetes mellitus.

One factor encouraging inflammatory diseases of the oral cavity is increased levels of plaque. This occurs, for example, due to the accumulation of food residues at sites that are less exposed to mechanical abrasion during chewing or teeth cleaning. Consequently, bacteria grow at higher rates in such regions, allowing for the formation of bacterial biofilms. Due to the embedding of minerals, the plaque may harden to form dental calculus.

As a result of bacteria settling in the region of the plaque, many different bacterial metabolic and catabolic products are released. The presence of such substances is a warning sign of a possible infection. The immune system of the colonised organism is capable of receiving these signs and triggering an appropriate defensive reaction. For this purpose, cells of the colonised organism can register the presence of these bacterial products by means of specific receptors on the cell surface. By way of many different cellular signal paths and appropriate cytokines, the warning sign is then relayed within the organism and specialised immune cells are recruited to fight the infection pathogens. For example, some immune cells can release particular chemical substances and enzymes that are capable of destroying bacteria.

Inter alia, periodontal diseases are known as inflammatory diseases of the oral cavity. These include, for example, inflammations of the periodontal apparatus (periodontium), referred to as periodontitis, or inflammations of the gums (gingivitis). In periodontitis, a distinction is generally drawn between marginal periodontitis, which starts from the gum line, and apical periodontitis, which starts from the tip of the tooth root. The prophylaxis and treatment of all these diseases is a critical area in dentistry.

According to current classifications of periodontal diseases, gingival diseases, chronic periodontitis, aggressive periodontitis, periodontitis as a manifestation of systemic diseases, necrotising periodontal diseases, abscesses in the periodontium, periodontitis in connection with endodontic lesions, and developmental or acquired deformations and conditions are included under the above term.

As periodontal diseases progress, an inflammatory reaction caused by bacteria generally spreads to many or even all parts of the periodontium. In the process, the periodontium tissue is destroyed and broken down.

Marginal periodontitis, for example, is an infection by specific strictly anaerobic or microaerophilic pathogens and is typically chronically recurrent. The most critical pathogens causing periodontitis are *Porphyromonas gingivalis, Tannerella forsythia, Aggregatibacter actinomycetemcomitans*, which are all gram-negative pathogens. These bacteria are also referred to as periodontitis marker bacteria. One consequence of such chronic infections is the slow loss of the periodontal connective tissue of the tooth (referred to as attachment loss); if the disease continues over the long term, the periodontal bone of the jaw alveolar bone is also lost.

Since it is in permanent contact with microorganisms, the periodontium is a very reactive tissue in immunological terms and exhibits a powerful response to the release of bacterial products by periodontitis pathogens. It should be explained that, unlike in infections in other body compartments, in periodontal diseases the tissue is mainly destroyed by the body's own immune reaction. This includes the breaking down of connective tissue by enzymes released by immune cells, e.g. metalloproteinases, and the breaking down of bone by osteoclasts being activated, which is promoted by prostaglandins, TNF-alpha and certain interleukins.

In addition, the periodontitis marker bacteria also produce virulence factors, which encourage the tissue-invasiveness of said bacteria and thus lead to local intensification in the inflammatory reaction. The body's own mechanisms, such as citrullination of proteins, further strengthen the immune reaction, which in turn increases the cell loss in the affected individual.

As prophylaxis for periodontal diseases, besides domestic oral hygiene, it is also recommended to have the teeth professionally cleaned; this serves to remove all plaque and/or calculus present as far as possible in order to keep the proinflammatory activation of the immune system within physiological limits or to prevent said activation.

In dentistry, periodontal diseases are treated using a number of approaches. Cleaning plaque from the tooth root and enamel by mechanical methods, even using ultrasound or lasers, is of major importance. In addition, antiseptics such as chlorhexidine can be introduced into the gingival sulcus by means of a blunt cannula or even using paper substrates (Periochip®). Moreover, antibiotics such as minocycline can be introduced into the gingival sulcus. This is often done using a carrier material that slowly degrades and releases the active ingredient steadily over this period.

For treatment to succeed in the long term, the above-described methods must be carried out repeatedly. However, since these methods are sometimes painful, in particular those based on mechanical cleaning, patients are often not particularly willing to regularly repeat these procedures, thereby reducing the success of the treatment.

The antiseptic or antibiotic treatment undertaken in certain cases concurrently with the removal of plaque and/or calculus does not specifically target the pathogens causing the periodontal disease, but rather they often damage the oral flora as a whole. As a result, the equilibrium of the oral flora may be adversely affected, resulting in high multiplication rates of certain microorganisms that are resistant to an antibiotic. This may encourage other infections. Furthermore, the use, and in particular long-term use, of antibiotics can lead to resistance in the microorganisms, which is currently one of the greatest threats to public health. Moreover, killing bacteria by means of antibiotics leads to the release of bacterial products, in particular catabolic products (bacterial toxins), which further intensify the body's own immune reaction, and thus in some circumstances also the destruction of tissue, and adversely impact on the physiological environment.

Against this background, the object of the present invention is to provide improved options for preventing and/or treating inflammatory conditions and/or diseases of the oral cavity, and in particular options that are gentler for patients.

This object is achieved by providing a composition that adsorbs bacterial products, preferably bacterial toxins, as part of the prevention and/or treatment of inflammatory conditions and/or diseases of the oral cavity. According to the invention, the composition contains the substance cholestyramine (poly(trimethylammonium methyl styrene chloride-co-divinylbenzene)), which comprises anion-exchange groups. These are suitable for adsorbing bacterial products, in particular toxic bacterial products such as lipopolysaccharides (LPS) and/or lipoteichoic acids (LTA).

As a result of this adsorption, firstly the toxic bacterial products are prevented from diffusing the centre of inflammation into adjacent regions. Secondly, the adsorption reduces the volume of the dissolved toxic bacterial products. This creates a condition for establishing the physiological environment and promotes and ensures a normal immune reaction.

The present invention thus provides options for neutralising proinflammatory bacterial products, in particular LPS and LTA, by means of binding. In the absence of such adsorption or neutralisation, the concentration of the dissolved toxic bacterial products is increased, which leads to an increase in tissue destruction by continuing to activate the immune system. A treatment approach of this kind has not been taken previously in periodontics.

It has also been found that beyond the adsorption or neutralisation, it is also possible to remove the toxic bacterial products from the inflammation site by removing the cholestyramine or cholestyramine-containing composition following application to the location of the inflammation.

The adsorption or neutralisation and/or removal of the toxic bacterial products from the inflammation site generally improves the conditions for natural regeneration processes. In addition, an approach of this kind results in the local immune reaction being down-regulated and thus leads to a significant reduction in tissue destruction, in particular by the body's own mechanisms. This is of major importance when treating periodontal diseases in particular since the periodontal connective tissue cannot be easily regenerated after being damaged.

In general, the composition used according to the invention can be used either alone or in combination with known preventive or treatment procedures. The use according to the invention of the adsorption agent cholestyramine is painless for the patient, unlike mechanical cleaning for example, and no side effects are expected. The substance has been known and widely used in medicine for 40 years to reduce blood cholesterol and to bind bile salts in the gut. Through regular application, the general success of the treatment is positively influenced, and so the treatment length can be reduced compared with that of treatment based solely on known treatment procedures. It can be assumed that these factors contribute to patients reliably persevering with a course of therapy prescribed by the doctor in charge. Therefore, providing the composition to treat diseases, in particular periodontal diseases, also improves patient compliance.

Moreover, when the adsorption agent is used according to the invention, a massive local release of toxic bacterial products can be prevented from crossing into the bloodstream and thus into the patient's body as a whole. This process can trigger the known cascade reaction, which advances in some cases in an autoimmune destructive manner due to the activation of mediators and can lead to septic manifestations and even to septic shock and death of the patient.

Nowadays, it is generally known that a link, at least a partial link, between periodontal disease and atherosclerosis (specifically coronary heart disease (CHD) and incidence of heart attack) is also based on the generalisation and chronicity of inflammations in the oral and dental region. Periodontal disease patients have a 25% higher risk of CHD compared with those with healthy teeth. The mortality of CHD patients is also twice as high in cases of periodontal disease compared with patients with healthy teeth.

Proinflammatory and pro-thrombotic inflammation mediators flushed into the bloodstream at higher rates due to a locally elevated bacterial load may act as the link between a chronic inflammation in the dental region and CHD. Here, the mediators may stimulate and maintain essential vascular-atherogenic processes, which ultimately lead to the closure of an artery.

There are preliminary results which point to the fact that removing chronic centres of inflammation (e.g. periodontal disease) also leads to normalisation of elevated inflammation mediators in the blood and tissue, increases the efficacy of statin therapy in reducing LDL and allows for a reduction in the required amounts of insulin in diabetes mellitus treatment.

It should therefore be expected that the application according to the invention of LPS and LTA adsorption materials in the oral region also leads, among other things, to a reduction in the heart attack rate among the population.

It has also been found that the use according to the invention of the adsorption agent does not interfere with the physiological defence and repair mechanisms of the organism. While the use according to the invention leads to the extremely effective removal of the harmful bacterial products, the physiological environment at the inflammation site is normalised, in particular in terms of the concentration ratios of the body's own mediators and cytokines, to the extent that the physiological healing processes can proceed unimpeded.

In general, an inflammatory condition of the oral cavity that can be treated in accordance with the present invention may result from an infection of or injury to the oral mucosa. In this case, possible infection pathogens are not only members of the natural oral flora, but also any microorganisms taken in via the mouth from the external environment.

In one embodiment, the inflammatory condition of the oral cavity results from a bacterial infection. In a preferred embodiment, the infection is one caused by gram-negative bacteria and/or gram-positive bacteria. In a particularly preferred embodiment, the infection is one caused by one or more bacteria selected from the group consisting of *Porphyromonas gingivalis, Tannerella forsythia* and *Aggregatibacter actinomycetemcomitans*.

If the immune defence system is generally weak, the development of a chronic infection locally may also be encouraged by injuries to the oral mucosa, whether incurred during chewing or any other injuries, including during operations.

In one embodiment, the disease of the oral cavity is a periodontal disease. In a preferred embodiment, the periodontal disease is marginal periodontitis. In a particularly preferred embodiment, the periodontal disease is selected from the group consisting of gingival diseases, chronic periodontitis, aggressive periodontitis, periodontitis as a manifestation of systemic diseases, necrotising periodontal diseases, abscesses in the periodontium, periodontitis in connection with endodontic lesions and/or developmental or acquired deformations and conditions. The agent used according to the invention for adsorbing bacterial products, in particular toxic bacterial products such as LPS and LTA, comprises anion-exchange groups. These are capable of selectively and effectively binding LPS and LTA and thus of absorbing them, neutralising them and possibly even removing them at the inflammation location.

It is advantageous if the cholestyramine adsorbing the LPS and/or LTA is well wetted at the site of use and the application surface area is as large as possible. Cholestyramine, which is already used to treat hypercholesterolaemia, to bind bile salts in the gut and for chronic diarrhoea, is provided as a substance in the form of a fine hygroscopic powder. It is a water-insoluble macromolecule that cannot be broken down by enzymes; it has been known in mainstream medicine for more than 40 years and cannot be resorbed in the gut, so it is not metabolised. Currently, it is available in the form of granules, powder or chewable tablets for peroral administration.

It is also possible to use the cholestyramine, present according to the invention in the composition, in combination with one or more additional active ingredients. There are no limits in terms of the selection of such additional active ingredients. A person skilled in the art may combine any additional active ingredients with the adsorption agent used according to the invention, as long as the intended efficacy of the adsorption agent is not thereby impaired such as to prevent the intended adsorption according to the invention of toxic bacterial products.

In a preferred embodiment, the one or more additional active ingredients are selected from the group consisting of antibacterial active ingredients, anti-inflammatory active ingredients, analgesic active ingredients, regenerative active ingredients or mixtures thereof. Particularly preferred in this case are antibiotics, silver ions, zinc oxide, povidone-iodine, activated carbon, ibuprofen, acetylsalicylic acid, diclofenac, local anaesthetics, e.g. lidocaine or benzocaine, dexpanthenol or mixtures thereof.

Conventional therapy for inflammatory conditions and/or diseases of the oral cavity often includes an antibiotic or antiseptic treatment, at least as an auxiliary measure. In most cases, antibiotic treatment does not act selectively against the pathogenic microorganisms that cause the disease being treated, but rather they also act against the natural oral flora. Harming the natural oral flora equilibrium normally present in the oral cavity can in turn have negative effects on the success of the therapy, for example by encouraging infections by opportunistic pathogens. In addition, in the case of antibiotic treatments, there is generally the problem of resistance development, which can impair the success of the therapy. Nonetheless, in the conventional treatment of inflammatory conditions and/or diseases of the oral cavity, it is often necessary to use antibiotics or other antibacterial active ingredients to assist the body's own immune system in fighting a pathogenic bacterial colonisation.

In the context of the present invention, by means of the use according to the invention of cholestyramine, it is often possible, due to the lower toxin load, to do away with the use of antibiotics or other antibacterial active ingredients, or largely reduce the use thereof.

Due to the use according to the invention of a composition containing cholestyramine, the body's own immune system is boosted. Under certain conditions, it is also conceivable, for example, to be able to reduce the death of immune cells by neutralising immunoactivating bacterial products and to thus make more immune cells available for fighting the bacterial pathogens. By means of this type of assistance, the immune system is able to better control the bacterial infection (elevated toxin load) and at least reduce the administration of antibiotics and/or other antibacterial agents when treating an inflammatory condition and/or a disease of the oral cavity.

It may also be possible to completely do away with the auxiliary use of antibiotics if the doctor in charge determines that the treatment is sufficiently likely to succeed through mechanical cleaning and/or the use of the composition according to the invention.

By doing away with the use of antibiotics and/or reducing the use thereof, it is possible to overcome or lessen the disadvantageous effects of these treatment options. In particular, the cholestyramine used according to the invention does not adversely influence the equilibrium of the oral flora, nor is the development of bacterial resistance to antibiotics boosted. In this respect, it should be noted in particular that development of resistance to the neutralisation according to the invention of toxic bacterial products cannot be expected.

In another embodiment of the present invention, and where necessary, cholestyramine can be used in the composition in combination with an antibiotic and/or antibacterial agents. Within the context of the present invention, it has been found that the treatment of inflammatory diseases of the oral cavity can also be positively influenced by such an approach.

While the targeted killing of bacteria helps fight the proinflammatory cause, it also leads to a massive release of toxic bacterial products, in particular when bactericidal agents are used.

In turn, these bacterial products intensify the body's own mechanisms that lead to tissue destruction. Contrary to the current situation, the composition used according to the invention can neutralise these bacterial products before the immune system can be (excessively) activated. This can prevent increased tissue destruction and/or prevent the healing process being impaired in any other way by the release of toxic bacterial products due to an antibiosis. In addition, the toxic bacterial products can also be prevented from crossing into the bloodstream and causing disadvantageous systemic effects up to septic shock, or, if the disease becomes chronic, prevented from leading to accelerated atherosclerosis, heart attack, diabetes mellitus or other illnesses having an inflammatory component.

Combining cholestyramine with antibacterial agents is particularly advantageous when using bactericidal agents and/or when bacterial density is high, as is the case in periodontal illnesses.

The composition used according to the invention can also be combined with products used for the care for, cleaning and/or treatment of the oral cavity. For example, cholestyramine can be used as an additive in teeth cleaning products such as toothpaste or tooth gel.

Due to the function of the salivary glands, the oral cavity has a constantly moist environment, and the surface of the oral cavity, in particular the oral mucosa and teeth surfaces, are generally constantly covered by a thin liquid film. When therapeutic agents are applied locally in the oral cavity, therefore, the problem generally arises whereby, after being applied, said agents are removed again from the application site by said liquid film and by mechanical rubbing generated by mouth movements. The resultant problem of the applied agent having an insufficient dwell time on the site being treated in each case can also arise during the use according to the invention of cholestyramine.

This problem can be overcome by using the composition used according to the invention in a form that can adhere to mucosa. This can preferably be achieved by using a composition having a viscous, paste-like or gel-like consistency. It is also possible for such a consistency to only be produced once the composition has been wetted. Wetting of this kind can be carried out by liquid present in the oral cavity, or by liquid to be applied from the outside.

In a particularly preferred embodiment, the composition of the invention comprises a gelling agent or is gel-based. Gelling agents of this kind are selected from the group consisting of alginates, polyacrylic acid, carboxymethyl cellulose, tragacanth, silicon dioxide, gelatine, methyl cellulose, poloxamers or povidone, but are not limited thereto. A person skilled in the art knows of other auxiliary agents suitable for this purpose, for example from reference books such as "Remington's Pharmaceutical Sciences".

The use of the above-described compositions specifically in the oral cavity is particularly advantageous since the aforementioned adhesion ability is boosted further by the confined spaces in certain application regions, e.g. in interdental spaces or gingival pockets. In this way, an even longer dwell time of the cholestyramine can be achieved in said locations. In periodontal diseases in particular, these application regions are especially relevant. The plaque causing the disease is also preferably formed at these sites.

Preferably, the composition according to the invention is provided in a pharmaceutical form selected from the group consisting of a paste, e.g. a toothpaste, a gel, e.g. a tooth gel, or a sprayable liquid, e.g. a spray. It is also possible to provide said composition using other materials such as hollow fibres, membranes, flat membranes, sponges, filter materials, particles, porous particles, beads, granules or powders to which cholestyramine is applied or with which it is mixed. These pharmaceutical forms can be provided in various applicators depending on the consistency, e.g. in dispensers or sprays, such as a spray nozzle or a powder spray. It is also possible to provide said composition in insert pads that are suitable for application in the mucosa region; pads of this kind can also be inserted into gingival pockets, for example.

In a preferred embodiment, the composition according to the present invention comprises cholestyramine in a concentration of from 5 wt. % to 50 wt. %, preferably from 5 wt. % to 40 wt. % or from 15 wt. % to 40 wt. %, or more preferably of around 15 wt. %, based on the total weight of the composition in each case.

Compositions according to the present invention can also comprise any known additional carrier materials and auxiliary agents.

In accordance with the present invention, the composition according to the invention can be applied in the mucosa region, in particular in the oral cavity, but also in other body regions. Particularly preferably, the composition can be used on the gums and/or gum line or the gingival sulcus. Particularly preferably, the composition is introduced into difficult-to-access sites in the oral cavity, e.g. gingival pockets or interdental spaces.

The composition according to the invention can be applied before, during and/or after other treatment procedures.

In addition to application for therapy purposes, the composition according to the invention can also be used prophylactically. It can be applied by the doctor in charge and/or the patient.

When using certain designs of the composition, it is not even necessary to remove these again via the mouth, e.g. by rinsing. The composition can also be removed via the digestive system. For this purpose, it is advantageous for cholestyramine to be sufficiently inert for the gastrointestinal tract and to not be resorbed, thereby ensuring very good biocompatibility.

When using an aforementioned design of the composition, in particular when using particles, porous particles, granules, powders, beads, membranes or hollow fibres, it is also possible to provide the adsorption agent used according to the invention or the pharmaceutical composition packed into small pouches or sachets. In doing so, it should be ensured that any material used for manufacturing such pouches or sachets is sufficiently permeable to the bacterial products being removed but still prevents the adsorption agent leaking out. Such pouches or sachets can be produced to a suitable size depending on the usage requirements. For example, pouches or sachets can be used in a size that the doctor in charge can introduce into the confined spaces of the oral cavity, e.g. the interdental spaces or gingival pockets. The pouches or sachets can be left at the treatment site for a sufficient amount of time to allow the toxic bacterial products to be bound. Subsequently, the doctor in charge can remove the pouches or sachets again, as a result of which the toxic bacterial products adsorbed in the meantime are also removed from the treatment site. The same also applies if the composition, as described above, is used in another design, e.g. in combination with any kind of membrane or pad. As well as use in human medicine, use in veterinary medicine is also provided.

The specific design of the composition according to the invention for use in the oral cavity is within the capabilities of a person skilled in the art; however, cholestyramine can be integrated in a toothpaste in a particularly simple manner, and this toothpaste can be used for prevention or treatment in daily oral hygiene. Therefore, the present invention also relates to a toothpaste of this kind containing cholestyramine as the active constituent, optionally combined with additional active ingredients.

The above-disclosed options for use of the agents and compositions according to the invention in the region of the oral cavity, in particular on the oral mucosa, can be carried across to applications in the female vaginal area in particular. In this region too, there is also a similarly moist environment as in the oral cavity, among other things, and infections or infected mucosa injuries are not as easily accessed as would be the case in superficial wounds.

Another area of application of the present invention is therefore the use in the prevention or in particular treatment of inflammatory conditions or diseases of the vaginal mucosa.

The invention claimed is:

1. A method for treating a periodontal disease, the method comprising applying a composition consisting of cholestyramine as an active agent to the oral mucosa of a subject afflicted with the periodontal disease, wherein the composition is left at the treatment site for sufficient amount of time to allow toxic bacterial products from bacteria causing the periodontal diease to be bound.

2. The method of claim 1, wherein composition is in the form of pouches or sachets.

3. The method of claim 2, wherein the toxic bacterial products comprise lipoteichoic acids, lipopolysaccharides, or combinations thereof.

4. The method of claim 2, wherein the pouches or sachets are sufficiently permeable to the toxic bacterial products but prevent the cholestyramine leaking out of the pouches or the sachets.

5. The method of claim 1, wherein the periodontal disease is a necrotising periodontal diseases.

6. The method of claim 1, wherein the periodontal disease is an abscess in the periodontium.

7. The method of claim 1, wherein the cholestyramine is provided as hollow fibres or a membrane to which cholestyramine is applied or with which it is mixed.

8. A method for treating a periodontal disease, the method comprising applying a composition consisting of cholestyramine as an active agent to the oral mucosa of a subject afflicted with the periodontal disease.

9. A method for treating a periodontal disease by applying a composition comprising cholestyramine to the oral mucosa of a subject afflicted with the periodontal disease;
wherein the composition comprises the cholestyramine in a concentration of from 5 wt. % to 50 wt. based on the total weight of the composition.

10. A method according to claim 9, wherein the periodontal disease is caused by a bacterial toxin selected from the group consisting of a lipopolysaccharides and a lipoteichoic acid.

11. A method according to claim 9, wherein the composition further comprises a gelling agent, or wherein the composition is gel-based.

12. A method according to claim 9, wherein the periodontal disease is periodontitis.

13. A method according to claim 12, wherein the composition has a viscous, pasty or gel consistency.

14. The method of claim 9, wherein the periodontal disease is selected from the group consisting of gingival diseases, chronic periodontitis, aggressive periodontitis, periodontitis as a manifestation of systemic diseases, necrotising periodontal diseases, abscesses in the periodontium, periodontitis in connection with endodontic lesions and/or developmental or acquired deformations and conditions.

15. The method of claim 9, wherein the periodontal disease is marginal periodontitis.

16. The method of claim 9, wherein the cholestyramine is in the form of granules or a powder.

17. The method of claim 9, wherein the cholestyramine is in the form of granules.

18. The method according to claim 12, wherein the composition has a pasty consistency.

19. The method according to claim 9, wherein the composition further comprises an antibacterial agent.

* * * * *